United States Patent [19]

Lucas et al.

[11] 4,234,317
[45] Nov. 18, 1980

[54] APPARATUS AND METHOD FOR FRACTIONATION OF LIPOPROTEINS

[75] Inventors: Flordeliza F. Lucas, Daly City; Ronald B. Smernoff, Belmont, both of Calif.

[73] Assignee: Analytical Products, Inc., Belmont, Calif.

[21] Appl. No.: 42,011

[22] Filed: May 24, 1979

[51] Int. Cl.³ .......................................... G01N 31/00
[52] U.S. Cl. ................................ 23/230 B; 23/909; 422/101; 210/927; 210/203; 210/205; 210/738
[58] Field of Search ................ 23/230 B, 909; 422/57, 422/59, 68, 100, 101, 102; 73/61.4; 435/11; 210/49, 52, 53, 73 R, 203, 204, 205, 219, 323 R, 324, 335, 332, DIG. 23, DIG. 24

[56] References Cited

U.S. PATENT DOCUMENTS

| 3,215,500 | 11/1965 | Bittner | 23/259 |
|---|---|---|---|
| 3,300,051 | 1/1967 | Mitchell | 210/339 |
| 3,319,792 | 5/1967 | Leder | 210/238 |
| 3,449,081 | 6/1969 | Hughes | 422/101 |
| 3,488,768 | 1/1970 | Rigopulos | 210/23 |
| 3,492,396 | 1/1970 | Dalton | 422/59 |
| 3,586,064 | 6/1971 | Brown | 141/1 |
| 3,630,683 | 12/1971 | Robb | 422/101 |
| 3,682,596 | 8/1972 | Stone | 23/253 R |
| 3,693,804 | 9/1972 | Grover | 210/359 |
| 3,721,528 | 3/1973 | Meed | 23/230 B |
| 3,761,408 | 9/1973 | Lee | 210/23 |
| 3,800,947 | 4/1974 | Smith | 210/359 |
| 3,807,955 | 4/1974 | Note | 23/230 B |
| 3,808,124 | 4/1974 | Dzlobkowski | 210/23 |
| 3,814,079 | 6/1974 | Le Roy | 23/259 |
| 3,870,639 | 3/1975 | Moore et al. | 210/359 |
| 3,882,716 | 5/1975 | Beiman | 73/61.4 |
| 3,901,808 | 8/1975 | Bokros | 210/263 |
| 3,905,895 | 9/1975 | Addis | 23/230 B |
| 3,953,172 | 4/1976 | Shapiro et al. | 23/230 B |
| 3,957,654 | 5/1976 | Ayres | 210/DIG. 23 |
| 3,963,119 | 6/1976 | Lukacs et al. | 210/DIG. 23 |
| 3,969,250 | 7/1976 | Farr | 210/359 |
| 3,970,518 | 7/1976 | Giaever | 23/230 B |
| 4,021,352 | 5/1977 | Sarstedt | 210/359 |
| 4,035,294 | 7/1977 | Landers | 210/77 |
| 4,040,959 | 8/1977 | Berman et al. | 210/78 |
| 4,053,284 | 10/1977 | Posch | 23/230 D |
| 4,057,499 | 11/1977 | Buono | 210/136 |
| 4,103,685 | 8/1978 | Lupien | 210/DIG. 23 |
| 4,123,224 | 10/1978 | Givner | 422/59 |
| 4,129,131 | 12/1978 | Naftulin | 210/DIG. 23 |

OTHER PUBLICATIONS

"High Density Liporprotein-Cholesterol", Environmental Chemical Specialties, Inc., Apr. 16, 1978.
CholOPAP-Advanced Bio-medical Methods, Inc., Aug., 1977.
SR-Plus Direct Cholesterol Test Set, Stanbio Laboratory, Inc., 1978.
HDL Reagent Set-Worthington Diagnostics, May, 1978.

*Primary Examiner*—Ernest G. Therkorn
*Attorney, Agent, or Firm*—Phillips, Moore, Weissenberger, Lempio & Majestic

[57] ABSTRACT

An apparatus and method for fractionating a liquid sample is disclosed. The liquid sample is generally blood plasma or blood serum from which it is desired to selectively remove low density lipoproteins while leaving behind high density lipoproteins. The apparatus comprises a chamber having a plurality of inert beads or particles in an upper portion thereof. The chamber is preferably defined by a disposable column. A dry reagent aliquot suitable for reacting with the liquid sample is coated upon the beads or particles. An upper filter is disposed in the chamber below the beads to retain the liquid sample during reaction. After reaction, the liquid sample is expressed through the upper filter and flows into a lower portion of the chamber. The lower portion includes a lower filter which separates low density lipoprotein containing flocculent from high density lipoprotein containing supernatant.

16 Claims, 2 Drawing Figures

APPARATUS AND METHOD FOR FRACTIONATION OF LIPOPROTEINS

BACKGROUND OF THE INVENTION

1. Field of the Invention

The present invention relates to an apparatus and method for fractionating a liquid sample, particularly a blood serum or plasma sample from which the low, very low, and ultra low density lipoproteins are to be removed.

2. Prior Art

It has recently been indicated that the level of high density lipoprotein cholesterol in a person's blood tends to be inversely related to the person's risk of coronary heart disease. Tests for high density lipoprotein cholesterol usually involve treatment of blood serum or plasma to remove the low, very low and ultra low density lipoproteins therefrom. This leaves the high density lipoprotein cholesterol in the serum or plasma sample, which may then be further treated for measurement of the high density lipoprotein cholesterol.

Measurements of high density lipoprotein in such samples are useful not only for study and prediction of coronary heart disease risk. Such measurements are also useful in conjunction with triglyceride and total cholesterol studies in the estimation of lipoprotein phenotypes.

To date, conventional techniques for effecting the separation of the low, very low and ultra low lipoprotein fractions from blood serum or plasma have involved centrifugation, frequently ultra centrifugation, electrophoresis, or high pressure liquid chromatography. Such prior art techniques have various disadvantages. Among the disadvantages are that relatively expensive equipment, apparatus or materials to effect separation have been required. The length of time necessary for performing separations, particularly in large scale testing laboratories, has frequently been inconveniently long. For example, the conventional centrifugation technique requires 30 to 45 minutes in the centrifuge. Further, the centrifuge should be of the expensive refrigerated type for good results. Finally, such prior art techniques have frequently required a sequence of steps such as pipetting, centrifugation and/or decanting which require care and skill of the technician performing the steps. Thus the disadvantages of prior art techniques have been that they are relatively slow and expensive and have required highly trained analysts and expensive equipment for their adequate performance.

As mentioned above, the importance of the relative amounts of high density and low density lipoprotein cholesterol as a diagnostic testing technique for detecting possible cardio-vascular problems, has been realized. Mass testing of patients on a regular basis, for these relative amounts is, thus, desirable. Yet, no inexpensive and rapid mass testing technique exists in the prior art for making the necessary analysis.

It is an object of the present invention to provide a rapid, simple and relatively inexpensive apparatus and method to achieve separation of the low, very low and ultra low lipoproteins from blood serum or plasma samples.

It is a further object of the present invention to provide such fractionated liquid samples ready for further analysis wherein any portion of a particular fractionated liquid sample may be analyzed to yield homogenous results.

SUMMARY OF THE INVENTION

In one aspect of the present invention, an apparatus for fractionating a liquid sample comprises a chamber and a means for retaining the sample to allow flocculent through reaction with a dry reagent aliquot on an inert surface and for allowing a supernatant to flow out of the chamber following the flocculation. The dry reagent aliquot is adapted to react with the liquid sample to form the flocculent and the supernatant.

In another aspect of the present invention, a method of fractionating a plasma or serum sample comprises the steps of adding, transferring and collecting. In the adding step, a predetermined volumetric range of plasma or serum blood sample is added to a first chamber having a surface coated with a substantially dry reagent aliquot to form a reacted plasma sample having a flocculent and a supernatant. In the transferring step, the reacted plasma sample is transferred from the first chamber to a second chamber. Finally, the supernatant is collected from the second chamber.

The present invention provides an apparatus which may be inexpensively manufactured, and provides a rapid method which obviates the pipetting, centrifugation and/or careful decantation steps of the prior art.

BRIEF DESCRIPTION OF THE DRAWINGS

Other objects and advantages of the present invention will become apparent from the following description and accompanying drawings wherein.

DETAILED DESCRIPTION OF THE PREFERED EMBODIMENTS

Figures 1, 2:
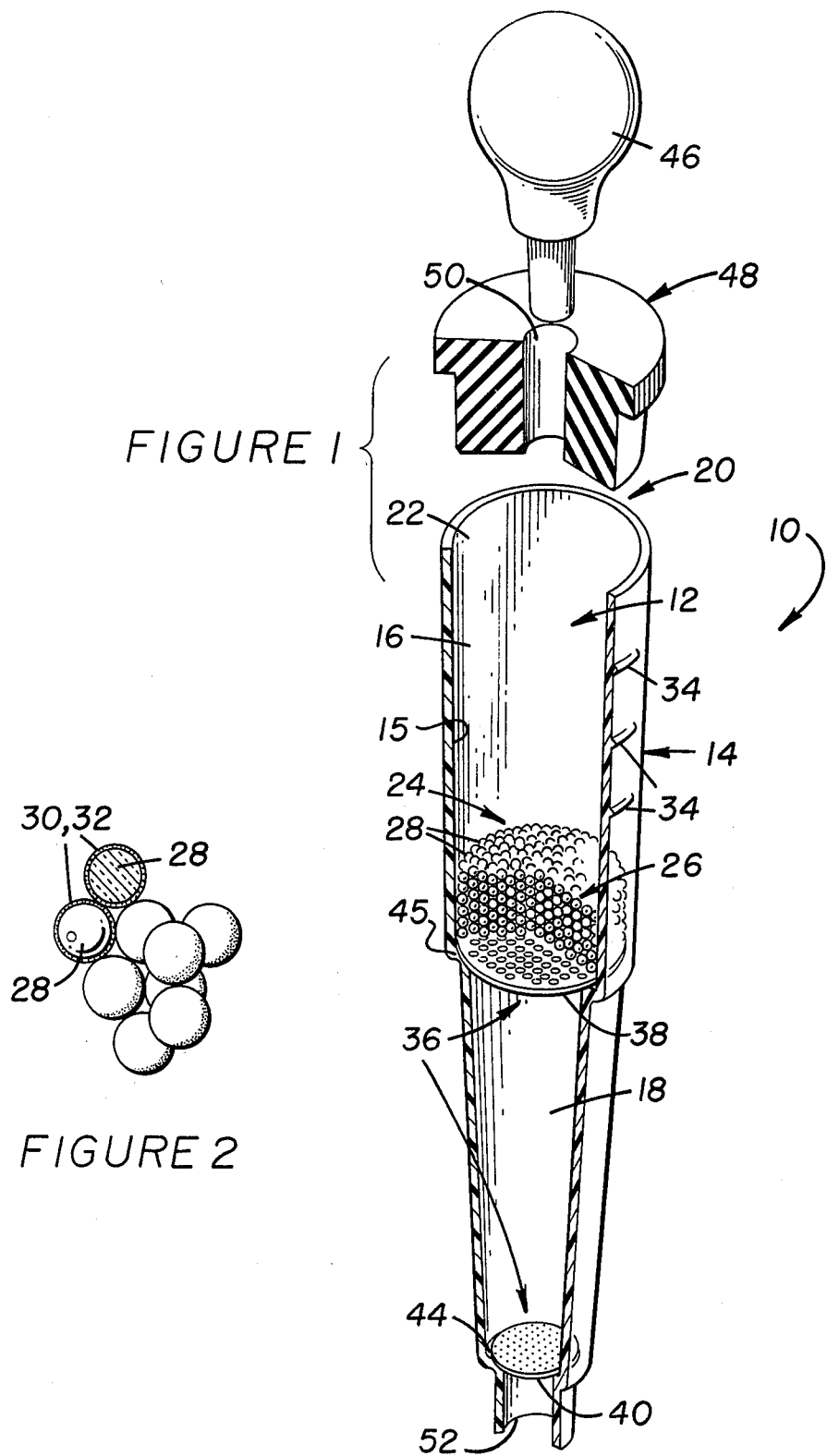
FIG. 1 is a perspective, exploded view of an embodiment of the present invention; and, FIG. 2 is an enlarged, cross-sectional view of a detail of the present invention.

Embodiments of the present invention are broadly applicable to a variety of liquid samples desirably fractionated, and are particularly useful for fractionating blood serum or blood plasma. The following detailed description will specifically discuss and use the word "plasma" for convenience to mean either blood plasma or blood serum.

When lipids circulate in blood they are combined with protein. These lipoproteins are classified into several groups. The classification depends on their separation in an ultra centrifuge. The ultra low density lipoproteins, or chylomicron density, are primarily triglycerides with little protein. The very low density lipoproteins are primarily triglycerides and cholesterol with increasing amounts of phospholipids and protein. The low density lipoproteins are primarily a complex of cholesterol and protein. The high density lipoproteins are primarily protein with cholesterol and phospholipids. Hereinafter, the ultra low, very low and low density lipoprotein fractions shall be collectively referred to as LDL cholesterol, whereas the high density lipoprotein fraction shall be referred to as HDL cholesterol.

Apparatus

Turning to FIG. 1, an apparatus 10 for fractionating a plasma sample comprises a chamber 12 defined within a generally transparent or translucent body, or longitudinally extending column 14, by a longitudinally extending inner wall 15. Column 14 is preferably disposable after use. A preferred material for column 14 is polypropylene which does not require pretreating to prevent adherence of the plasma sample to inner wall 15, and which may be inexpensively manufactured in great quantities by processes such as injection molding or the like.

Chamber 12 has an upper portion 16 and a lower portion 18. The upper portion 16 has plasma admitting means 20 for admitting plasma into the upper portion 16 of chamber 12. Means 20 may simply be an open mouth 22 of the column 14.

The upper portion 16 has an inert surface 24 which carries a substantially dry reagent aliquot 26 thereon. The function of the inert surface 24 is to maximize the surface area exposure of the reagent aliquot 26 to the plasma sample when it has been admitted into the upper portion 16 of chamber 12. The reagent aliquot 26 is substantially dry in order that the plasma sample is not diluted when exposed thereto and, even more importantly, so that no liquid is added to the plasma, which could introduce possible operator error and require eventual back calculation from the HDL cholesterol content of the supernatant to that of the plasma. It is clear that no matter what size plasma sample is introduced to the upper portion 16, the concentration of a dissolved component which does not react with the dry reagent aliquot 26 is substantially the same after contact with the dry reagent aliquot 26 as it was before such contact.

The inert surface 24 may be simply the wall of the upper portion 16 with the reagent aliquot 26 coated thereon. More preferably, the inert surface 24 is the surface of a plurality of inert members, more specifically a plurality of substantially spherical beads or other particles 28 within upper portion 16. When the inert surface 24 is the beads or particles 28, then they primarily function to maximize the surface area exposure of dry reagent 26, but also aid somewhat in homogeneously mixing the dry reagent 26 for dissolving into the plasma sample when column 14 is shaken or agitated. The beads 28 are preferably of about 1200 mesh, being shown enlarged for convenient illustration by FIG. 1. An excellent material for the beads 28 is glass, on which the dry reagent aliquot 26 may be readily coated, or adsorbed as further hereinafter described. The dry reagent aliquot 26 is adapted to react with the plasma sample to form a flocculent and a supernatant as follows.

Referring to FIG. 2, such adaptation for a plasma sample is where the dry reagent aliquot 26 includes two dry components 30 and 32. The component 30 is a compound providing a divalent cation. The component 32 is a compound providing a polyvalent anion.

The component 30 may be anyone of a variety of compounds providing the divalent cation. However, the chloride salts of magnesium, manganese and barium are particularly suitable compounds for the component 30, as chloride does not interfere with subsequent analysis of the plasma sample after it has been reacted in and collected from chamber 12.

The component 32 may be any one of a variety of compounds providing the polyvalent anion, such as polyols, mucopolysaccharides, and polysaccharides. Sodium dextron sulfate and heparin are particularly suitable compounds for the component 32.

The reaction of plasma with heparin and manganese chloride to precipitate, or flocculate, the LDL cholesterol is known and is more fully described in an article by P. S. Bachorik, et al entitled "Plasma High-Density Lipoprotein Cholesterol Concentrations Determined after Removal of Other Lipoproteins by Heparin/Manganese Chloride Precipitation or by Ultra Centrifugation", which appears in *Clinical Chemistry*, Volume 22, beginning at page 1828, published in 1976. Accordingly, the particular chemical reactions of the plasma sample are herein summarily described as follows.

A plasma sample, which has an LDL cholesterol content and a HDL cholesterol content, when added to the dry reagent aliquot 26, yields a reacted plasma sample having a flocculent and a supernatant. The flocculent is substantially all the LDL cholesterol and the supernatant is substantially all the HDL cholesterol when the dry reagent aliquot 26 is of sufficient quantity to drive the plasma sample reaction to completion. That is, the LDL cholesterol is substantially depleted from the supernatant.

Thus, it is necessary that the dry reagent aliquot 26 be at least of a predetermined, minimum quantity, which quantity ensures that the dry reagent aliquot 26 is in excess of that necessary to react with all the LDL cholesterol in the plasma sample. The plasma sample is within a predetermined, volumetric range which is sufficiently small with respect to the quantity of reagent aliquot 26 to ensure that the HDL and LDL cholesterol concentrations will be the limiting factors in the reaction. The range of HDL in samples is usually from about 25 to about 65 mg/dl, with the combined HDL and LDL cholesterol in plasma samples being from about 135 to about 350 mg/dl.

Returning to FIG. 1, the predetermined, volumetric range of plasma sample for reaction within upper portion 16 of chamber 12 is preferably from about 0.5 ml to about 2.0 ml. The column 14 may have inscribed, or printed thereupon, volumetric indicia 34 for convenience of use thereof. For such volumes of sample, sufficient minimum quantity of the dry reagent aliquot 26 is where the component 30 is about 94 millimoles, and the component 32 is about 226 International Units (when it is heparin).

A coating of components 30 and 32 with excipients is evaporatively deposited upon the beads or particles 28 with constant agitation. The components 30 and 32 are simply dissolved in any mutual solvent which is non-deleterious to them and reasonably volatile, the beads or particles 28 are placed in the resulting solution, and the solvent is evaporated away with constant agitation. Water is generally used as the solvent, but ethanol and other alcohols can be used, or any other convenient mutual solvent for the components 30 and 32.

Referring to FIG. 1, the apparatus 10 of the present invention further comprises means 36 for retaining the plasma sample in the presence of the inert surface 24, more particularly in the presence of beads 28, for a time sufficient to completely react with the dry reagent aliquot 26 and also for allowing the supernatant to flow out of the chamber 12 after the reaction therein is substantially complete. The means 36 preferably includes an upper filter 38 or other holding means and a lower filter 40, although a single filter of proper strength and properties, or a valve (as holding means in place of the upper filter 38) followed by the lower filter 40 are as contemplated as being usable. The advantage of using the upper filter 38 and lower filter 40 is that the former can be made quite rugged to support the beads 28, even with agitation. The lower filter 40 must have relatively fine holes to retain the flocculent and such filters are generally not strong enough to support the beads 28 and withstand expression forces as are discussed below.

The lower filter 40 is disposed in the chamber 12, more particularly in the lower portion 18 thereof, and is of sufficient construction to retain the flocculent while permitting the supernatant to flow therethrough. Such sufficient construction is where lower filter 40 is positioned transversely in chamber 12 with respect to the longitudinal extension of column 14 and includes a plurality of micropores therethrough, the pores preferably being in the range of about 0.5 micron to about 100 micron. Good results have been obtained with a lower filter 40 having nominally 45 micron pores. The wall 15 of the lower portion 18 of chamber 12 may be formed as a stepped bore and hence define a shoulder 44. The lower filter 40 may conveniently positioned, after insertion, into chamber 12 to rest upon shoulder 44.

The upper filter 38 is interposed between the lower filter 40 and the inert surface 24, or beads 28. In effect, the upper filter 38 is the transition of chamber 12 from the upper portion 16 to the lower portion 18 and is positioned transversely in chamber 12 with respect to the longitudinal extension of column 14. Such positioning may be where the wall 15 of upper portion 16 is formed as a stepped bore and hence defines a shoulder 45 on which upper filter 38 rests. The desirable functions of upper filter 38 include acting as a support for the beads 28, as well as retaining the plasma sample in the upper portion 16 until the reaction between the plasma sample and the components 30,32 of reagent aliquot 26 is substantially complete. The upper filter 38 is also of sufficient construction to then allow at least some of the flocculent and the supernatant to flow from the upper portion 16 into the lower portion 18. Such flow is preferably in response to a selected force being imposed upon the flocculent and supernatant in the upper portion 16.

The selected force for imposition upon the flocculent and supernatant is preferably only slightly greater than one gravitational force, and may be imposed quite simply by means such as a rubber bulb 46. The rubber bulb 46 may be used to discharge a quantity of gas into the upper portion 16 to cause part or all of the flocculent and substantially all of the supernatant to flow, or be expressed, through the upper filter 38 (or other holding means) and into the lower portion 18 of chamber 12. The open mouth 22 of column 14 is normally closed by a plug 48 which has an orifice 50 therethrough adapted to receive the air discharged by bulb 46.

METHOD

A method of fractionating the plasma sample comprises the steps of adding, transferring and collecting which are described as follows.

As previously described, the plasma sample has a LDL cholesterol content and an HDL cholesterol content. A predetermined, volumetric range of this sample is added to a first chamber, such as the upper portion 16, defined by a body such as disposable column 14. The first chamber, or upper portion, 16 has a surface, such as the inert surface 24, which is coated with a substantially dry reagent aliquot 26 having components 30 and 32. Inert surface 24 is preferably a plurality of inert beads or particles 28 coated as previously described. The predetermined, volumetric range of the sample is sufficiently small for the reagent aliquot 26 to substantially completely flocculate the LDL cholesterol and to form a reacted plasma sample including a flocculent and a supernatant. As previously noted, the flocculent has substantially all of the LDL cholesterol while the supernatant has substantially all of the HDL cholesterol and is substantially depleted of LDL cholesterol. Such a sufficiently small predetermined volumetric range is preferably from about 0.5 ml. to about 2 ml.

After the plasma sample has been substantially completely reacted, the transferring and collecting steps are performed. However, it is preferred that, after the plasma sample has been added to the first chamber 16 and before the transferring step, the plasma sample be agitated. Such agitation may be readily and rapidly accomplished by placing the column 14 having the first chamber, or upper portion, 16 in a conventional vortex type mixer set at medium speed. The dry reagent aliquot 26 is mixed with the plasma sample until a homogenous appearing solution is obtained. When beads or particles 28 are present, they aid in the agitation. Immediately following such agitation, the method preferably further comprises waiting a sufficient time, generally at least about 5 minutes, before proceeding to the transferring step. Such waiting permits sufficient time for the plasma sample to substantially completely react, and may be accomplished by simply placing the column 14 on a conventional stand with the column 14 being substantially vertical and the first chamber, or upper portion 16, being upwardly orientated.

Turning to the transferring step, the reacted plasma sample is then transferred from the first chamber 16 to a second chamber having flocculent separating means therein. Such a second chamber may simply be the previously described lower portion 18 of chamber 12, and the flocculent separating means may simply be the lower filter 14. Such transferring is preferably accomplished without the necessity of pipetting or decanting the reacted plasma sample from the first chamber 16 into the second chamber 18. Thus, where the first and second chambers are the upper and lower portions 16,18 of a single column 14, and include a flow preventing means with the flow retaining and permitting functions previously described for upper filter 38, the transferring is quite simply accomplished by expressing the reacted plasma sample through the upper filter 38 by means such as the rubber bulb 46.

The flocculent separating means is preferably simply the lower filter 40 as previously described which retains the flocculent and permits the supernatant to flow therethrough. When utilizing the apparatus 10 in the herein described method, the supernatant is collected from the second chamber, or lower portion 18 quite simply, as the supernatant drains from the lower filter 40 by gravity and collection from an open tip 52 of the chamber 12 may be into any one of a variety of sample collection vessels placed therebeneath.

The supernatant collected as above described has substantially all of the HDL cholesterol of the initial plasma sample and is substantially depleted of all the LDL cholesterol. This supernatant, after collection, may be taken directly for analysis, and is uniform in composition from start to finish through the flocculent separating means, or lower filter 40. Hence the entire quantity of supernatant does not need to be collected before measurement of the HDL cholesterol content is begun. Part or all of the supernatant collected as above described may be stored up to one week under refrigeration (from about 2° to about 6° C.), or may be stored in a frozen form for up to about one month.

While the invention has been described in connection with specific embodiments thereof, it will be understood that it is capable of further modification, and this application is intended to cover any variations, uses or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

What is claimed is:

1. An apparatus for fractionating a liquid sample having low density and high density lipoprotein contents, said sample being within a predetermined volumetric range, comprising:
   a column defining a chamber having first and second portions;
   a plurality of inert members having a large surface area within said first portion of said chamber;
   a substantially dry reagent aliquot coated on the surfaces of said inert members, said dry reagent aliquot being adapted to react with said low density lipoprotein content and form a flocculent therefrom and to not react with said high density lipoprotein content and to thereby produce a supernatant having a substantially unchanged high density lipoprotein concentration; and
   means (1) for retaining said liquid sample in the presence of said inert members and said aliquot for a time sufficient to react with said aliquot said means for retaining said liquid sample being of sufficient construction to allow substantially all of said supernatant to flow from said first portion of said chamber in response to a selected force being imposed upon said supernatant while retaining said inert members, and (2) means for separating said flocculant from said supernatant in response to flowing of said supernatant from said first portion of said chamber.

2. The apparatus as in claim 1 wherein said inert members are loosely disposed within said chamber.

3. The apparatus as in claim 2 wherein said inert members are glass beads of about 1200 mesh particle size.

4. The apparatus as in claim 2 wherein said dry reagent aliquot includes a plurality of components.

5. The apparatus as in claim 1 or 4 wherein:
   said means includes a lower filter disposed in said chamber and being of sufficient construction to retain said flocculent thereon while permitting said supernatant to flow therethrough.

6. The apparatus as in claim 5 wherein:
   said means includes an upper holding means interposed between said lower filter and said inert surface and defining said first portion as an upper portion and said second portion as a lower portion of said chamber, said upper portion having said inert surface and said lower portion having said lower filter.

7. The apparatus as in claim 6, wherein said upper holding means is an upper filter.

8. The apparatus as in claim 7 wherein:
   said upper filter is of sufficient construction to allow at least part of said flocculent and substantially all of said supernatant to flow from said upper portion to said lower portion in response to a selected force being imposed upon said flocculent and supernatant.

9. The apparatus as in claim 8 further comprising:
   means for discharging a quantity of gas into said upper portion for providing said selected force sufficient to cause said flocculent and said supernatant to flow through said upper filter and into said lower portion.

10. The apparatus as in claim 2 wherein said dry reagent aliquot includes a pair of chemicals.

11. A method of fractionating a plasma or serum blood sample comprising:
    adding said sample having a low density lipoprotein content and a high density lipoprotein cholesterol content to a first chamber within a column, said first chamber having a plurality of inert members having a large surface area coated with a substantially dry reagent aliquot, said sample being within a predetermined volumetric range sufficiently small for said reagent aliquot to substantially completely flocculate said low density cholesterol and to form a reacted plasma sample including a flocculant having substantially all of the low density lipoprotein cholesterol and a supernatant of substantially unchanged high density lipoprotein cholesterol concentration and being substantially low density lipoprotein cholesterol depleted;
    transferring said reacted plasma sample from said first chamber to a second chamber, said second chamber having flocculant separating means therein; and
    collecting said supernatant which has been separated from said flocculant from said second chamber.

12. The method as in claim 11 wherein:
    said first and second chambers are upper and lower portions of a single column, said upper and lower portions being separated by flow preventing means, and said transferring step comprises applying sufficient gas pressure to said upper portion to force said supernatant and at least part of said flocculent to flow past said flow preventing means to said lower portion.

13. The method as in claim 11 or 12 further comprising:
    waiting at least about 5 minutes after said adding step and before said transferring step.

14. The method as in claim 13 further comprising:
    agitating said sample, after said adding step and before said waiting step, sufficiently to homogenously mix said sample with said dry reagent aliquot.

15. The method as in claim 11 further comprising, prior to said adding step coating said dry reagent aliquot upon a plurality of inert particles; and
    loosely placing said inert particles in said first chamber.

16. The method as in claim 11, further including:
    analyzing said collected supernatant to determine the high density lipoprotein cholesterol concentration of said supernatant and of said sample.

* * * * *